(12) United States Patent
Yamaji et al.

(10) Patent No.: US 12,092,776 B2
(45) Date of Patent: Sep. 17, 2024

(54) RADIATION DETECTOR AND PRODUCTION METHOD FOR RADIATION DETECTOR

(71) Applicant: HAMAMATSU PHOTONICS K.K., Hamamatsu (JP)

(72) Inventors: Haruki Yamaji, Hamamatsu (JP); Kazuhiro Shirakawa, Hamamatsu (JP); Keisuke Goto, Hamamatsu (JP); Masashi Hatanaka, Hamamatsu (JP); Jun Sakurai, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 0 days.

(21) Appl. No.: 17/766,564

(22) PCT Filed: Jul. 9, 2020

(86) PCT No.: PCT/JP2020/026856
§ 371 (c)(1),
(2) Date: Apr. 5, 2022

(87) PCT Pub. No.: WO2021/079568
PCT Pub. Date: Apr. 29, 2021

(65) Prior Publication Data
US 2024/0103188 A1    Mar. 28, 2024

(30) Foreign Application Priority Data

Oct. 24, 2019    (JP) .................................. 2019-193424

(51) Int. Cl.
*G01T 1/20*    (2006.01)
*G01T 1/202*    (2006.01)

(52) U.S. Cl.
CPC ........ *G01T 1/20188* (2020.05); *G01T 1/2002* (2013.01); *G01T 1/202* (2013.01)

(58) Field of Classification Search
CPC .... G01T 1/20188; G01T 1/2002; G01T 1/202
See application file for complete search history.

(56) References Cited

U.S. PATENT DOCUMENTS

| 2008/0142721 | A1 | 6/2008 | Spahn | |
|---|---|---|---|---|
| 2011/0198505 | A1* | 8/2011 | Ishida | ..................... G01T 1/202 250/363.01 |
| 2012/0112075 | A1* | 5/2012 | Noda | .................... G01T 1/2002 250/361 R |

FOREIGN PATENT DOCUMENTS

| CN | 103728650 A | 4/2014 |
|---|---|---|
| EP | 1365261 B1 | 12/2016 |

(Continued)

OTHER PUBLICATIONS

International Preliminary Report on Patentability mailed May 5, 2022 for PCT/JP2020/026856.

*Primary Examiner* — Kiho Kim
(74) *Attorney, Agent, or Firm* — Faegre Drinker Biddle & Reath LLP (57) ABSTRACT

A radiation detector includes: a sensor panel; a scintillator panel; and a resin frame provided across the sensor panel and the scintillator panel, in which the sensor panel has a mounting surface where the scintillator panel is mounted, the scintillator panel includes a support body having a first surface, a second surface on a side opposite to the first surface, and a first side surface connecting the first surface and the second surface to each other, and a scintillator layer formed on the first surface and containing a plurality of columnar crystals, the scintillator panel is mounted on the mounting surface such that the scintillator layer and the first surface face the mounting surface, and the scintillator layer has a second side surface extending so as to be positioned on the same plane as the first side surface.

14 Claims, 6 Drawing Sheets

(56) References Cited

FOREIGN PATENT DOCUMENTS

| | | | |
|---|---|---|---|
| JP | 2002-341039 | A | 11/2002 |
| JP | 2010-256373 | A | 11/2010 |
| JP | 2011-011805 | A | 1/2011 |
| JP | 2012-047723 | A | 3/2012 |
| JP | 2012-118058 | A | 6/2012 |
| JP | 2013-217913 | A | 10/2013 |
| JP | 2016-095189 | A | 5/2016 |
| JP | 2019-060876 | A | 4/2019 |
| JP | 2019-095289 | A | 6/2019 |
| TW | 201409062 | A | 3/2014 |
| TW | 201638611 | A | 11/2016 |

\* cited by examiner

RADIATION DETECTOR AND PRODUCTION METHOD FOR RADIATION DETECTOR

TECHNICAL FIELD

The present disclosure relates to a radiation detector and a radiation detector manufacturing method.

BACKGROUND ART

A radiation detector is described in Patent Literature 1. This radiation detector includes a support body, a scintillator layer laminated inside the outer edge of the support body, a photodetector substrate attached to the scintillator layer and forming a gap with the support body, and a sealing film. The gap is filled with the sealing film. The film thickness of the middle portion of the sealing film is smaller than the film thickness of the end portion of the sealing film.

CITATION LIST

Patent Literature

Patent Literature 1: Japanese Unexamined Patent Publication No. 2012-118058

SUMMARY OF INVENTION

Technical Problem

In the radiation detector described above, the scintillator layer is made dampproof by the sealing film, with which the gap between the support body and the photodetector substrate is filled. In the radiation detector described above, the middle portion of the sealing film in particular has a relatively small film thickness. Accordingly, the sealing film is likely to be elastically deformed by following the warpage of the support body and the photodetector substrate. In addition, the film thickness of the end portion of the sealing film is relatively large, and thus adhesion is ensured between the sealing film and the support body and the photodetector substrate and dampproofness is retained.

In other words, in making the scintillator layer dampproof in the radiation detector described above, it is essential to form the scintillator layer smaller than the support body and fill the gap between the support body, the scintillator layer, and the photodetector substrate with the sealing film having the characteristics described above. Accordingly, the effective area of scintillator layer formation becomes smaller than the size of the support body.

An object of the present disclosure is to provide a radiation detector and a radiation detector manufacturing method enabling reliability to be ensured and an increase in effective area to be achieved at the same time.

Solution to Problem

A radiation detector according to the present disclosure includes: a sensor panel; a scintillator panel; and a resin frame provided across the sensor panel and the scintillator panel, in which the sensor panel has a mounting surface where the scintillator panel is mounted, the scintillator panel includes a support body having a first surface, a second surface on a side opposite to the first surface, and a first side surface connecting the first surface and the second surface to each other, and a scintillator layer formed on the first surface and containing a plurality of columnar crystals, the scintillator panel is mounted on the mounting surface such that the scintillator layer and the first surface face the mounting surface, the scintillator layer has a second side surface extending so as to be positioned on the same plane as the first side surface, and the resin frame is configured to seal the scintillator layer by extending at least from the mounting surface onto the first side surface when viewed in a first direction intersecting with the first side surface and the second side surface.

In this radiation detector, the scintillator panel is mounted on the sensor panel such that the scintillator layer faces the mounting surface of the sensor panel. As for the scintillator panel in particular, the first side surface as the side surface of the support body and the second side surface as the side surface of the scintillator layer are positioned on the same plane. In other words, the scintillator layer is provided on the entire surface of the support body when viewed in the direction intersecting with the first surface and the second surface of the support body and an increase in effective area is achieved as a result. In such a configuration, the boundary between the support body and the scintillator layer and the boundary between the scintillator layer and the sensor panel are prone to lateral damage. On the other hand, in this radiation detector, the resin frame extends at least from the mounting surface of the sensor panel onto the first side surface of the support body, and thus the scintillator layer is sealed. Accordingly, damage to the boundary and the second side surface as the side surface of the scintillator layer can be avoided. At the same time, the dampproofness of the scintillator layer is improved and peeling attributable to a difference in thermal expansion and warpage is suppressed. In other words, with this radiation detector, reliability is ensured while an increase in effective area is achieved as described above.

In the radiation detector according to the present disclosure, the support body may have a first flexible support body having the first surface and a third surface on the side opposite to the first surface, a second flexible support body having the second surface and a fourth surface on a side opposite to the second surface, and an inorganic layer provided between the third surface and the fourth surface, and the resin frame may seal the inorganic layer by extending at least from the mounting surface to the fourth surface when viewed in the first direction. In this case, the inorganic layer suppresses moisture infiltration from the second surface side into the scintillator layer via the first flexible support body. In particular, the dampproofness is reliably improved by the resin frame extending beyond the inorganic layer (so as to reach the fourth surface). Further, the second flexible support body protects the inorganic layer from contact and suppresses deterioration of the inorganic layer. As a result, reliability is reliably ensured.

In the radiation detector according to the present disclosure, the resin frame may extend from the mounting surface to a peripheral edge portion of the second surface. In this case, the dampproofness is further improved, the peeling is reliably suppressed, and reliability is ensured more reliably.

In the radiation detector according to the present disclosure, the resin frame may include an inner edge positioned on the second surface and an outer edge positioned outside the second surface when viewed in a second direction intersecting with the second surface, and a distance from the inner edge of the resin frame to a peripheral edge of the second surface may be twice or less a distance from the peripheral edge of the second surface to the outer edge. In this case, reliability can be reliably ensured and a decrease in effective area can be suppressed at the same time.

In the radiation detector according to the present disclosure, the resin frame may include a plurality of parts arranged along the first side surface and the second side surface and may include at least one overlapping portion where one of the parts and another of the parts overlap. In this manner, the resin frame may be configured by the plurality of parts.

In the radiation detector according to the present disclosure, a ratio of a width of the resin frame from the first side surface may be 0.1 or more and 12.5 or less when a height of the resin frame from the mounting surface is 1. In this case, reliability can be ensured and an increase in size can be avoided at the same time.

The radiation detector according to the present disclosure may include an adhesive layer interposed between the mounting surface and the scintillator panel and bonding the sensor panel and the scintillator panel to each other. In this case, the scintillator panel and the sensor panel are joined with high accuracy.

In the radiation detector according to the present disclosure, the resin frame may contain a filler material made of an inorganic material. In this case, the dampproofness is further improved.

In the radiation detector according to the present disclosure, the resin frame may contain at least a pigment having reflectivity or absorbency with respect to scintillation light generated by the scintillator layer. In this case, optical characteristics are improved.

In the radiation detector according to the present disclosure, a protective layer may be formed on the mounting surface. In this case, the reliability of the sensor panel is improved.

In the radiation detector according to the present disclosure, the scintillator panel may include a protective layer formed on the first side surface and the second side surface. In this case, lateral damage and moisture infiltration can be suppressed more reliably.

A radiation detector manufacturing method according to the present disclosure includes: a first step of preparing a scintillator panel having a support body and a scintillator layer formed on the support body; a second step of preparing a sensor panel including a photoelectric conversion element; a third step of mounting the scintillator panel on the sensor panel such that the scintillator layer faces the sensor panel; and a fourth step of providing a resin frame across the sensor panel and the scintillator panel after the third step, in which the support body has a first surface where the scintillator layer is formed, a second surface on a side opposite to the first surface, and a first side surface connecting the first surface and the second surface to each other, the scintillator layer has a second side surface extending so as to be positioned on the same plane as the first side surface, the sensor panel has a mounting surface where the scintillator panel is mounted, and, in the fourth step, the resin frame is formed by resin application and curing being performed with respect to at least the mounting surface, the first side surface, and the second side surface and so as to seal the scintillator layer by extending at least from the mounting surface onto the first side surface when viewed in a first direction intersecting with the first side surface and the second side surface.

In this manufacturing method, the scintillator panel is mounted on the sensor panel such that the scintillator layer faces the mounting surface of the sensor panel. As for the scintillator panel in particular, the first side surface as the side surface of the support body and the second side surface as the side surface of the scintillator layer are positioned on the same plane. In other words, the scintillator layer is provided on the entire surface of the support body when viewed in the direction intersecting with the first surface and the second surface of the support body and an increase in effective area is achieved as a result. In such a configuration, the boundary between the support body and the scintillator layer and the boundary between the scintillator layer and the sensor panel are prone to lateral damage. On the other hand, in this manufacturing method, the resin frame is formed so as to seal the scintillator layer by extending at least from the mounting surface of the sensor panel onto the first side surface of the support body. Accordingly, damage to the boundary and the second side surface as the side surface of the scintillator layer can be avoided. At the same time, the dampproofness of the scintillator layer is improved and peeling attributable to a difference in thermal expansion and warpage is suppressed. In other words, by this manufacturing method, it is possible to manufacture the reliable radiation detector while achieving an increase in effective area as described above.

In the radiation detector manufacturing method according to the present disclosure, in the fourth step, the resin frame may be formed by the resin application and curing being performed a plurality of times. In this case, the overlapping portion of the plurality of parts configuring the resin frame can be formed by the resin being applied and cured after the resin is applied and cured once.

In the radiation detector manufacturing method according to the present disclosure, in the fourth step, the resin frame may be formed by the resin application and curing being performed using a mold disposed on the mounting surface so as to surround the scintillator panel while being separated from the scintillator panel when viewed in a second direction intersecting with the second surface. In this case, the generation of a sagging portion of the resin can be suppressed.

In the radiation detector manufacturing method according to the present disclosure, in the third step, the scintillator panel may be mounted on the sensor panel via an adhesive layer.

Advantageous Effects of Invention

According to the present disclosure, a radiation detector and a radiation detector manufacturing method enabling reliability to be ensured and an increase in effective area to be achieved at the same time can be provided.

DESCRIPTION OF EMBODIMENTS

Hereinafter, one embodiment will be described in detail with reference to the drawings. In the description of the drawings, the same or corresponding elements may be denoted by the same reference numerals with redundant description omitted.

The radiation detector (radiation imager) according to the present embodiment converts radiation such as X-rays into scintillation light such as visible light and detects (images) the light. In addition, the radiation detector according to the present embodiment can be used in, for example, a medical X-ray diagnostic imaging apparatus such as a mammography apparatus, a chest examination apparatus, a CT apparatus, a dental intraoral imaging apparatus, and a radiation camera and a non-destructive inspection apparatus.

Figure 1:
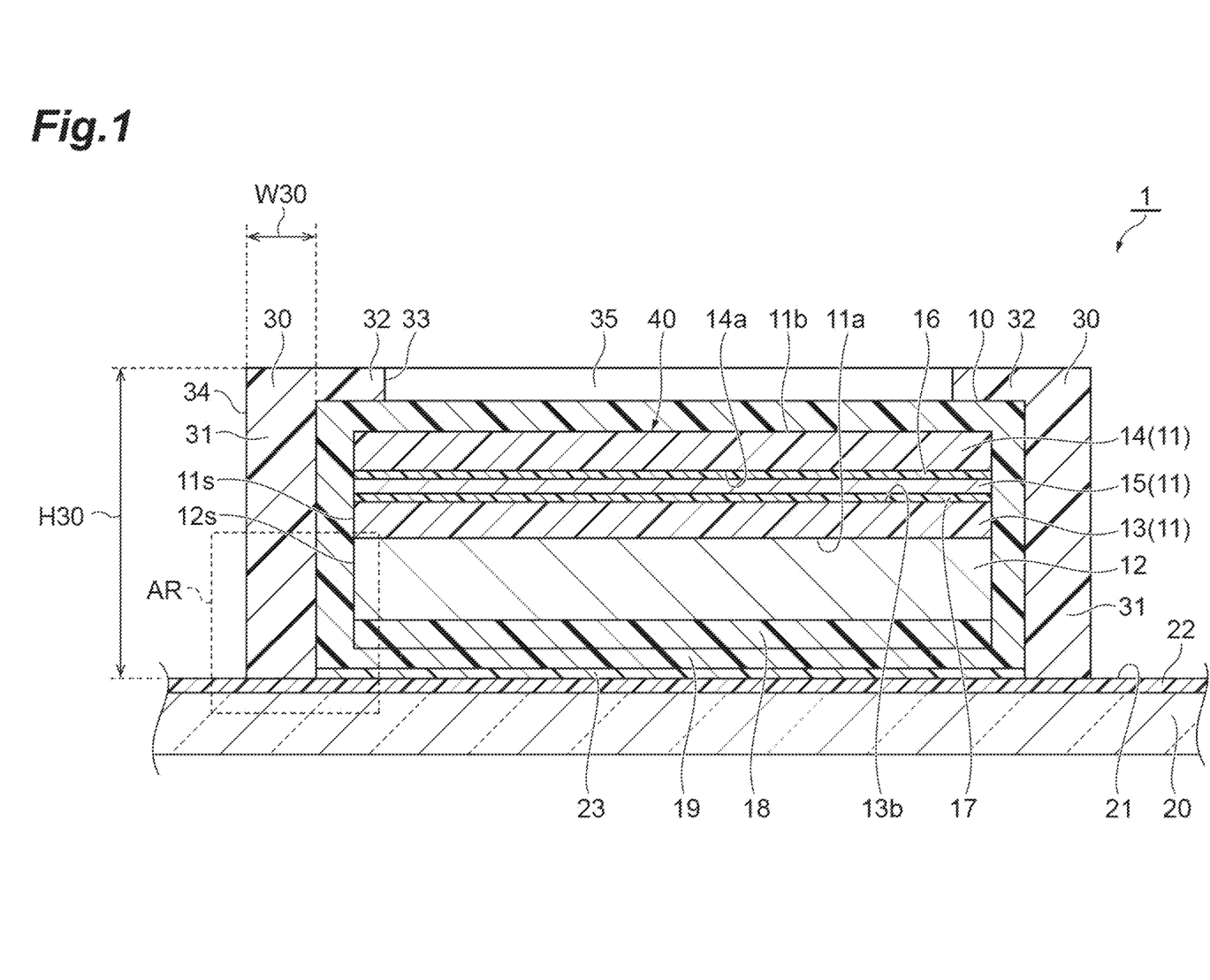
FIG. 1 is a schematic cross-sectional view illustrating a radiation detector according to the present embodiment.

FIG. 1 is a schematic cross-sectional view illustrating the radiation detector according to the present embodiment. As illustrated in FIG. 1, a radiation detector 1 includes a scintillator panel 10, a sensor panel 20, and a resin frame 30. The scintillator panel 10 includes a support body 11, a scintillator layer 12, a protective layer 18, and a protective layer 19.

The support body 11 is formed in a flat plate shape here and has a first surface 11a, a second surface 11b on the side opposite to the first surface 11a, and a first side surface 11s connecting the first surface 11a and the second surface 11b to each other. The first surface 11a and the second surface 11b are parallel to each other.

The scintillator layer 12 is formed on the first surface 11a. The scintillator layer 12 generates scintillation light in response to radiation incidence from the second surface 11b side. The scintillator layer 12 contains a plurality of columnar crystals. As an example, the scintillator layer 12 is made of a plurality of columnar crystals. The scintillator layer 12 is suitable for high-resolution imaging by each columnar crystal having a light guide effect.

Examples of the material of the scintillator layer 12 include a material containing cesium iodide (CsI) as a main component such as CsI:Tl and CsI:Na, a material containing sodium iodide (NaI) as a main component such as NaI:Tl, strontium iodide ($SrI_3$), lutetium iodide ($LuI_3$), barium fluoride (BaF2), and GOS. Here, the material of the scintillator layer 12 is a material containing CsI as a main component. The scintillator layer 12 can be formed by, for example, an evaporation method. The thickness of the scintillator layer 12 is, for example, 10 μm or more and 3000 μm or less. As a specific example, the thickness is 600 μm.

The scintillator layer 12 has a second side surface 12s. The second side surface 12s connects one surface of the scintillator layer 12 in contact with the support body 11 and another surface on the side opposite to the one surface. The second side surface 12s is positioned on the same plane as the first side surface 11s of the support body 11. In other words, the first side surface 11s and the second side surface 12s are substantially flush with each other. As an example, when the first side surface 11s and the second side surface 12s are formed as cut surfaces at a time when the support body 11 and the scintillator layer 12 are cut together by a blade, laser light irradiation, or the like, the first side surface 11s and the second side surface 12s are substantially flush with each other. Accordingly, the first side surface 11s and the second side surface 12s may have fine uneven structures such as rough surfaces and burrs when viewed microscopically and yet those uneven structures can be ignored when defined as "flush". As an example, the first side surface 11s and the second side surface 12s extend perpendicularly to the first surface 11a and the second surface 11b of the support body 11.

Here, the support body 11 includes a first flexible support body 13, a second flexible support body 14, an inorganic layer 15, and adhesive layers 16 and 17. The first flexible support body 13 includes the first surface 11a of the support body 11. In addition, the first flexible support body 13 includes a third surface 13b on the side opposite to the first surface 11a. The second flexible support body 14 includes the second surface 11b of the support body 11. In addition, the second flexible support body 14 includes a fourth surface 14a on the side opposite to the second surface 11b. In other words, in the support body 11, the first surface 11a, the third surface 13b, the fourth surface 14a, and the second surface 11b are arranged in order from the scintillator layer 12 side.

The first flexible support body 13 and the second flexible support body 14 are flexible. It should be noted that being flexible means being elastically deformable. As a result, the support body 11 is flexible as a whole. Examples of the materials of the first flexible support body 13 and the second flexible support body 14 include polyethylene terephthalate (PET), polyethylene naphthalate (PEN), polyimide (PI), polypropylene (PP), polyethylene (PE), and acrylic (PMMA). As an example, the materials of the first flexible support body 13 and the second flexible support body 14 are PET, PEN, PI, PP, PE, or PMMA. Here, the materials of the first flexible support body 13 and the second flexible support body 14 are PET. In addition, the material of the first flexible support body 13 and the material of the second flexible support body 14 are, for example, the same. It should be noted that the first flexible support body 13 may have an anchor coat layer made of a thermoplastic resin (e.g. acrylic) on the forming surface of the scintillator layer 12 so that adhesiveness is enhanced in relation to the scintillator layer 12. When the scintillator layer 12 is configured by a plurality of columnar crystals in particular, the crystallinity of the roots of the columnar crystals is improved by the anchor coat layer.

The inorganic layer 15 is provided between the third surface 13b and the fourth surface 14a. The inorganic layer 15 is provided on the second flexible support body 14. The second flexible support body 14 provided with the inorganic layer 15 is bonded to the third surface 13b of the first flexible support body 13 by the adhesive layer 17. In other words, the adhesive layer 17 bonds the third surface 13b and the inorganic layer 15 to each other.

The adhesive layer 16 is interposed between the inorganic layer and the second flexible support body 14. The inorganic layer 15 is bonded to the second flexible support body 14 by the adhesive layer 16. In other words, the adhesive layer 16 bonds the inorganic layer 15 and the second flexible support body 14 to each other. In this manner, the scintillator layer 12, the first flexible support body 13, the inorganic layer 15, and the second flexible support body 14 are laminated in this order to form a laminated body 40 and are integrated by the adhesive layers 16 and 17.

The inorganic layer 15 is made of an inorganic material. As an example, the material of the inorganic layer 15 is a metal. More specifically, examples of the material of the inorganic layer 15 include aluminum (Al), copper (Cu), titanium (Ti), iron (Fe), and SUS. As an example, the material of the inorganic layer 15 is Al.

The thickness of the first flexible support body 13 in a second direction intersecting with the first surface 11a (and the second surface 11b) is, for example, 50 μm or more and 250 μm or less. Likewise, the thickness of the second flexible support body 14 in the second direction is, for example, 50 μm or more and 250 μm or less. The difference between the thickness of the first flexible support body 13 and the thickness of the second flexible support body 14 is, for example, 0 or more and 90 μm or less. As an example, the thickness of the first flexible support body 13 is equal to the thickness of the second flexible support body 14 (the difference in thickness is 0). The thickness of the inorganic layer 15 in the second direction is, for example, 10 µm or more and 100 µm or less. The thickness is smaller than the thickness of the first flexible support body 13 and the thickness of the second flexible support body 14. The thickness of the inorganic layer 15 is, for example, 30 µm.

The protective layer 18 is provided on the surface of the scintillator layer 12 on the side opposite to the support body 11. The protective layer 19 is provided so as to cover the laminated body 40 (that is, the support body 11 and the scintillator layer 12) and the protective layer 18. As a result, the plurality of (two here) protective layers 18 and 19 are disposed on the surface of the scintillator layer 12 on the side opposite to the support body 11. In addition, the protective layer 19 is formed on the first side surface 11s of the support body 11 and the second side surface 12s of the scintillator layer 12. The material of the protective layers 18 and 19 is, for example, an organic material such as a resin, examples of which include parylene (polyparaxylene).

The sensor panel 20 includes a photoelectric conversion element. The sensor panel 20 detects the scintillation light generated by the scintillator panel 10 and outputs a signal corresponding to the scintillation light. The sensor panel 20 has a mounting surface 21. A protective layer 22 is formed on the mounting surface 21. Examples of the material of the protective layer 22 include an oxide film, a nitride film, a fluorine-based resin, and an aromatic resin. It should be noted that the protective layer 22 may not be formed.

The scintillator panel 10 is mounted on the mounting surface 21 via the protective layer 22. More specifically, the scintillator panel 10 is mounted on the mounting surface 21 such that the first surface 11a of the support body 11 and the scintillator layer 12 face the mounting surface 21. An adhesive layer 23 is interposed between the scintillator panel 10 and the mounting surface 21 (protective layer 22). The scintillator panel and the sensor panel 20 are bonded to each other by the adhesive layer 23. It should be noted that the adhesive layers 16, 17, and 23 can be configured by any adhesive and sticky material, examples of which include a tape-shaped adhesive material (double-sided tape).

Figure 2:
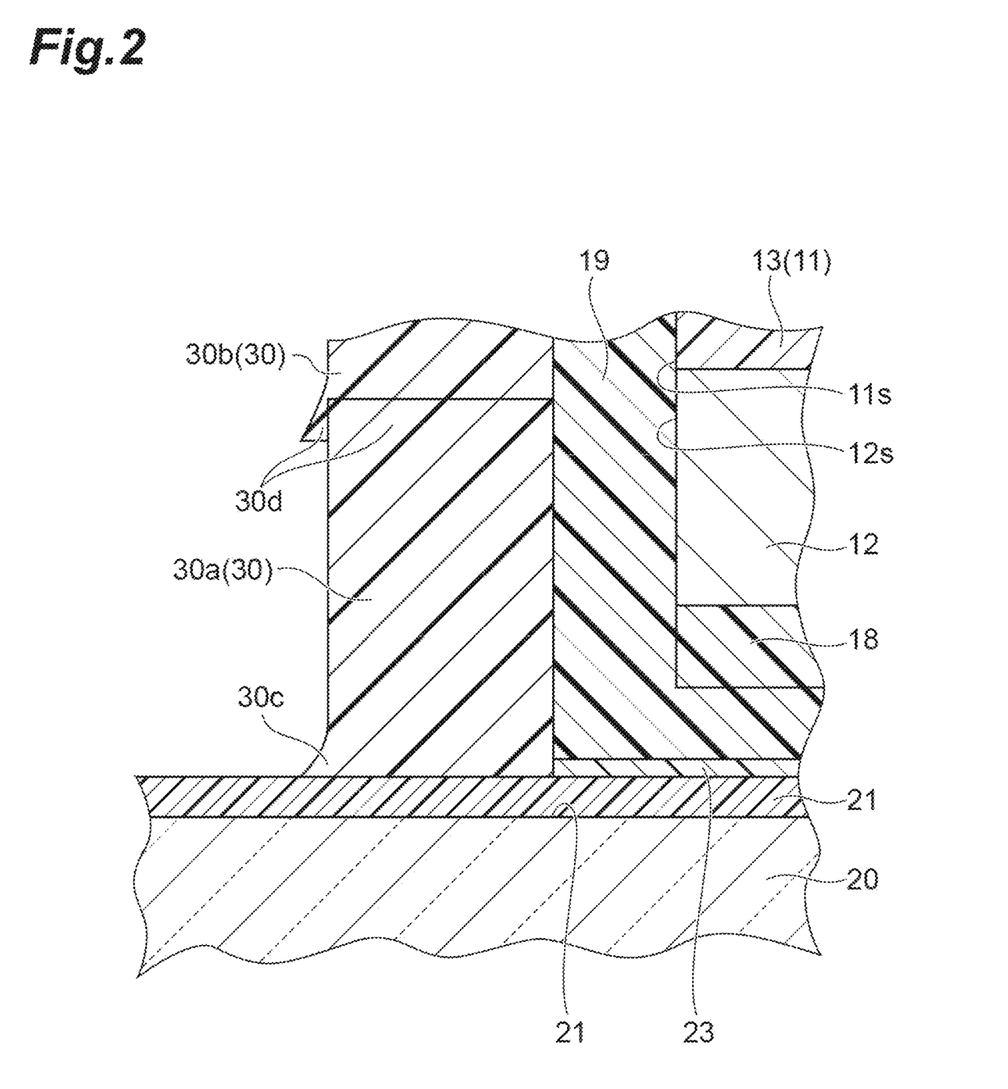
FIG. 2 is an enlarged view of a region AR of FIG. 1.
Figure 3:
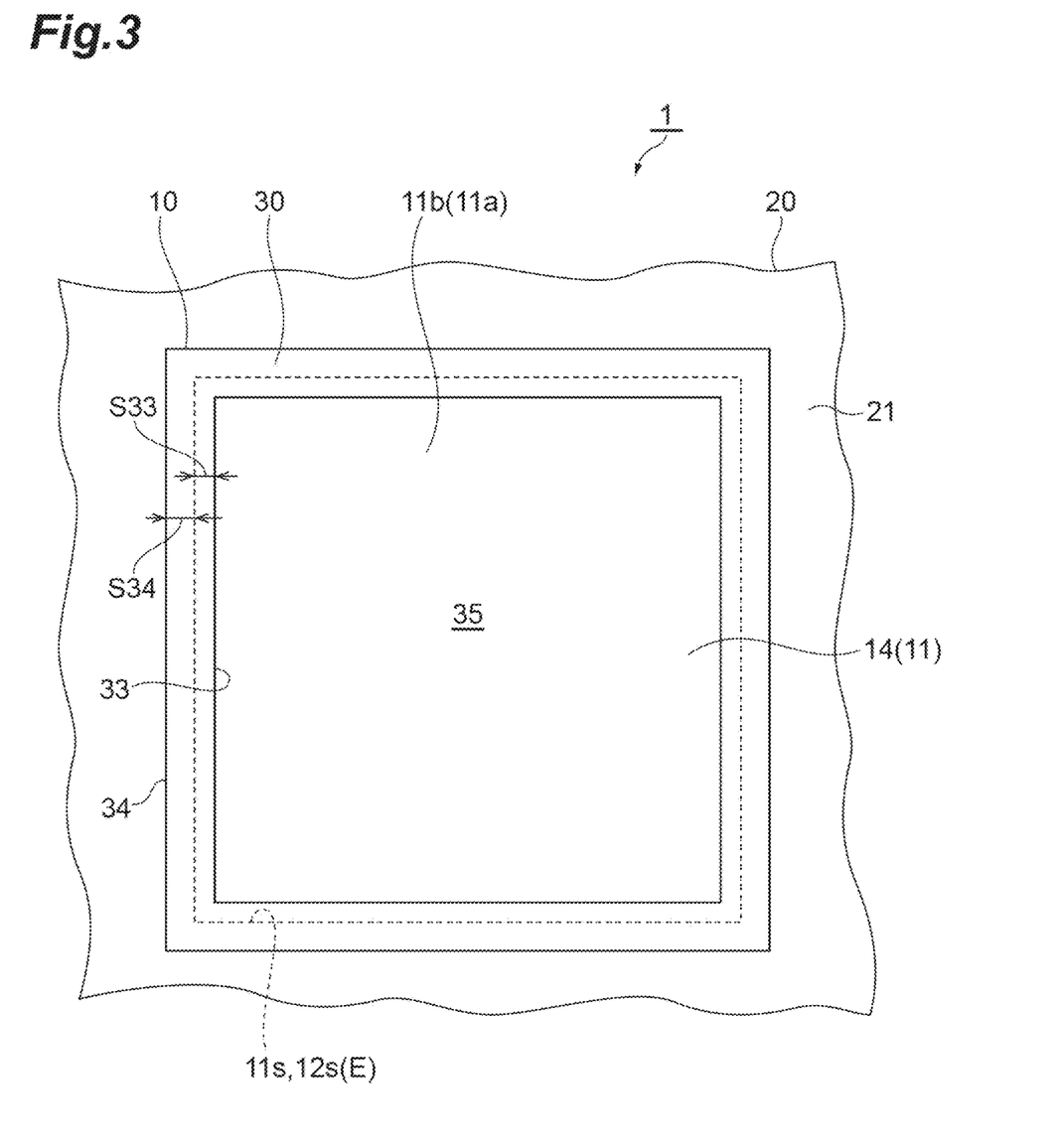
FIG. 3 is a schematic plan view of the radiation detector illustrated in FIG. 1.

The resin frame 30 is provided across the sensor panel 20 and the scintillator panel 10. The resin frame 30 will be described in detail below. FIG. 2 is an enlarged view of a region AR of FIG. 1, and FIG. 3 is a schematic plan view of the radiation detector illustrated in FIG. 1. In FIG. 3, the protective layers 18 and 19 are omitted. As illustrated in FIGS. 1 to 3, the resin frame 30 seals the scintillator layer 12 by extending from the mounting surface 21 onto the first side surface 11s when viewed in a first direction intersecting with the first side surface 11s of the support body 11 and the second side surface 12s of the scintillator layer 12.

The resin frame 30 is in close contact with (that is, may be partially separated from) the first side surface 11s, the second side surface 12s, and the mounting surface 21 on most of the first side surface 11s, the second side surface 12s, and the mounting surface 21. As a result, the resin frame 30 contributes to fixing the scintillator panel 10 and the sensor panel 20. Here, the resin frame 30 also seals the inorganic layer 15 by extending from the mounting surface 21 to the fourth surface 14a of the second flexible support body 14 when viewed in the first direction.

Further, here, the resin frame 30 extends from the mounting surface 21 to the peripheral edge portion of the second surface 11b beyond the fourth surface 14a. In other words, the resin frame 30 includes a main body portion 31 extending along the first side surface 11s and the second side surface 12s and an extending portion 32 extending from the main body portion 31 onto the second surface 11b. Here, the main body portion 31 covers the entire first and second side surfaces 11s and 12s.

The resin frame 30 is formed in an annular shape when viewed in the second direction intersecting with the first surface 11a and the second surface 11b and has an inner edge 33 positioned on the second surface 11b. In other words, the resin frame 30 forms an opening portion 35 on the second surface 11b without covering most of the second surface 11b. The inner edge 33 is the end portion of the extending portion 32 on the side opposite to the main body portion 31. In addition, the resin frame 30 has an outer edge 34 positioned outside the second surface 11b when viewed in the second direction. The outer edge 34 is the end portion of the main body portion 31 on the side opposite to the extending portion 32.

A distance S33 from the inner edge 33 of the resin frame 30 to a peripheral edge E of the second surface 11b (first and second side surfaces 11s and 12s) is twice or less a distance S34 from the peripheral edge E of the second surface 11b to the outer edge 34. When a height H30 of the resin frame 30 from the mounting surface 21 is 1, the ratio of a width W30 of the resin frame 30 (main body portion 31) from the first side surface 11s and the second side surface 12s is 0.1 or more and 12.5 or less. The height H30 is, for example, 200 µm or more and 2500 µm or less. The width W30 is, for example, 300 µm or more and 2500 µm or less.

Here, the resin frame 30 may be configured by a plurality of parts. More specifically, as illustrated in FIG. 2, the resin frame 30 includes a plurality of parts arranged along the first side surface 11s and the second side surface 12s. In this case, the resin frame 30 may include at least one overlapping portion 30d where one part 30a and another part 30b overlap. In the overlapping portion 30d, the width W30 of the resin frame 30 may be enlarged as compared with other parts (that is, the overlapping portion 30d may be a widened portion). In addition, a widened portion 30c can be similarly formed at the boundary part of the resin frame 30 in relation to the mounting surface 21. The widened portion 30c can be formed even when the resin frame 30 is configured by a single part.

The material of the resin frame 30 is, for example, epoxy, silicon, fluorine, urethane, acrylic, or the like. The resin frame 30 is capable of containing, for example, a filler material made of an epoxy resin or an inorganic material such as glass. The material of the filler material may be more dampproof than the main material of the resin frame 30 and is, for example, $SiO_2$, $Al_2O_3$, $TiO_2$, or the like. In addition, the resin frame 30 may contain at least a pigment having reflectivity or absorbency with respect to the scintillation light generated by the scintillator layer 12.

Figure 4:
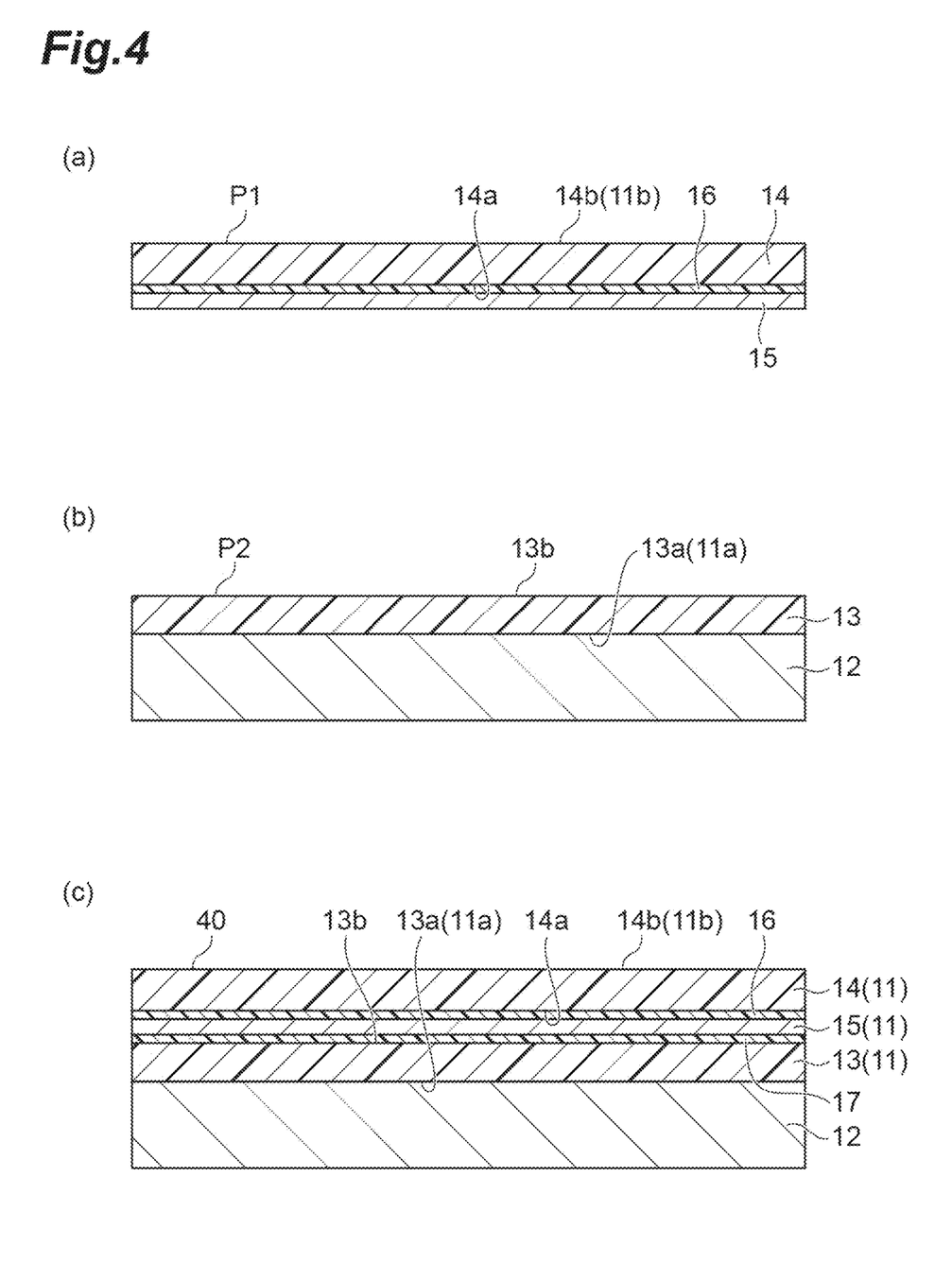
FIG. 4 is a schematic cross-sectional view illustrating one step of a method for manufacturing the radiation detector illustrated in FIGS. 1 to 3.
Figure 5:
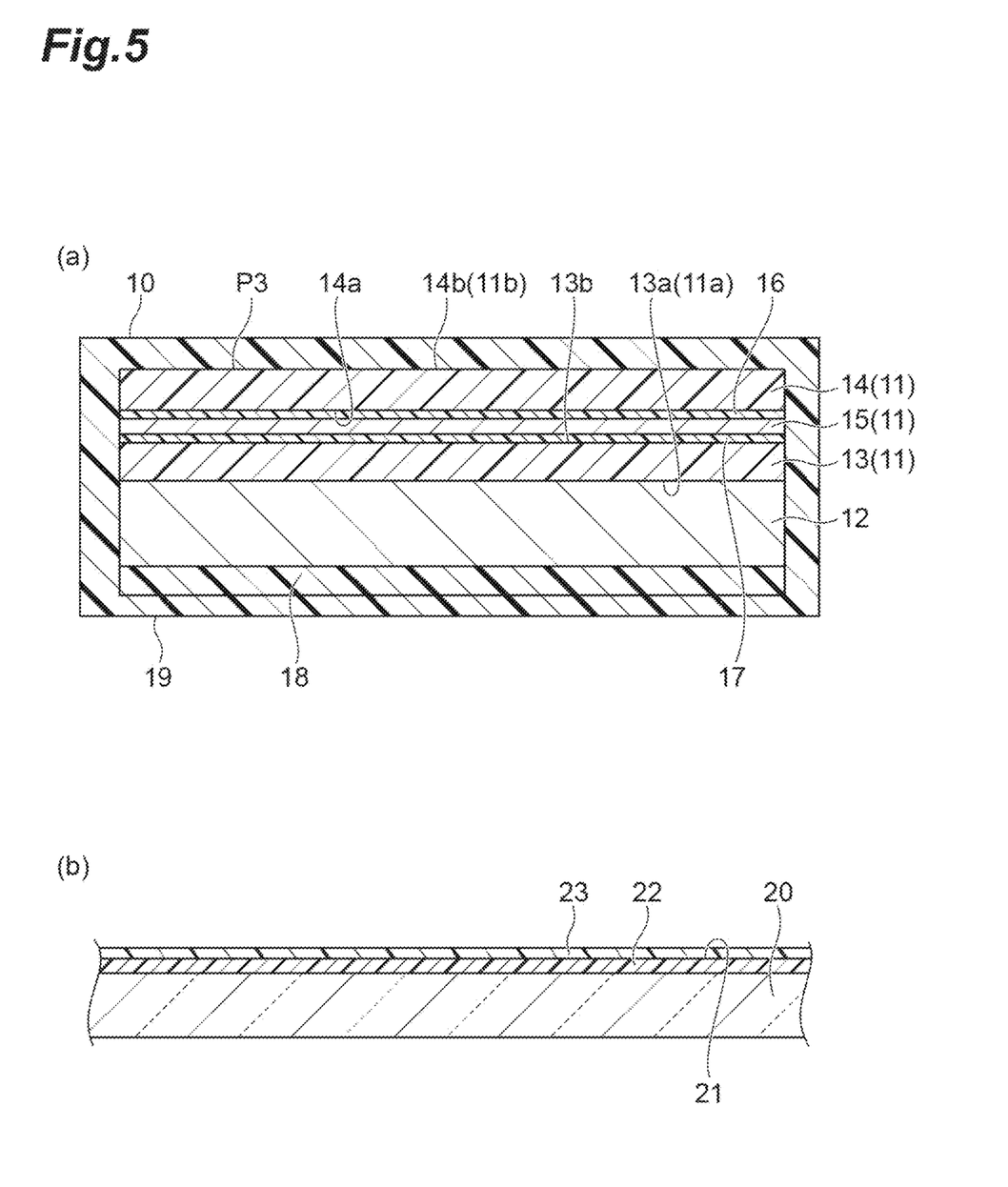
FIG. 5 is a schematic cross-sectional view illustrating one step of the method for manufacturing the radiation detector illustrated in FIGS. 1 to 3.
Figure 6:
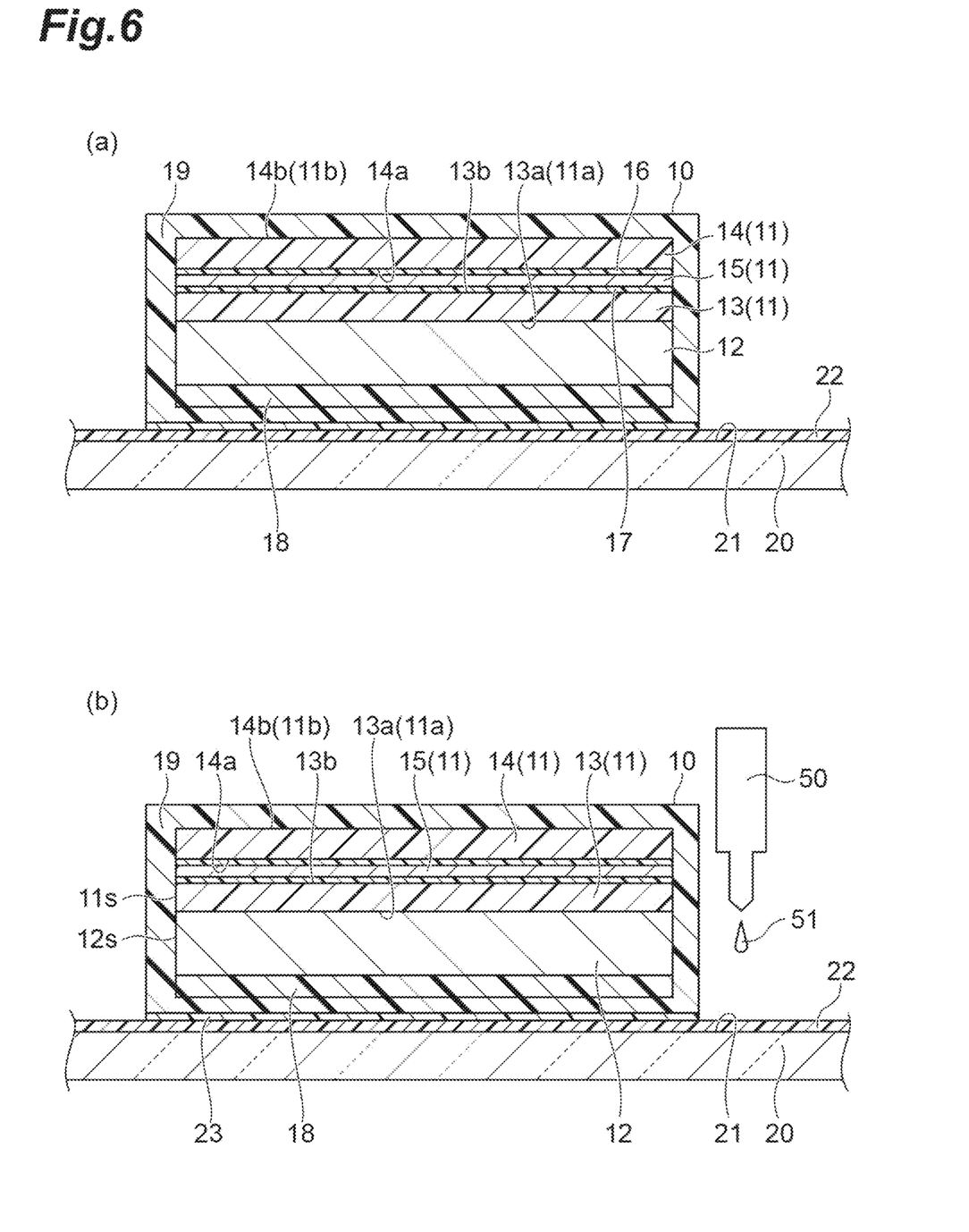
FIG. 6 is a schematic cross-sectional view illustrating one step of the method for manufacturing the radiation detector illustrated in FIGS. 1 to 3.

A method for manufacturing the above radiation detector will be described below. FIGS. 4, 5, and 6 are schematic cross-sectional views illustrating one step of the method for manufacturing the radiation detector illustrated in FIGS. 1 to 3. As illustrated in FIGS. 4 to 6, in the method for manufacturing the radiation detector 1 according to the present embodiment, a first step of preparing the scintillator panel 10, a second step of preparing the sensor panel 20, a third step of mounting the scintillator panel 10 on the sensor panel 20, and a fourth step of forming the resin frame 30 across the scintillator panel 10 and the sensor panel 20 are carried out. It should be noted that the first step and the second step may be carried out in any order.

As illustrated in FIG. 4(a), in the first step, a fifth step of configuring a first structure P1 by bonding the inorganic layer 15 to the fourth surface 14a of the second flexible support body 14 with the adhesive layer 16 is carried out. A surface 14b of the second flexible support body 14 on the side opposite to the fourth surface 14a is the surface that becomes the second surface 11b of the support body 11. Meanwhile, as illustrated in FIG. 4(b), in the first step, a sixth step of configuring a second structure P2 by forming the scintillator layer 12 on a surface 13a of the first flexible support body 13 by, for example, an evaporation method is carried out. The surface 13a is the surface that becomes the first surface 11a of the support body 11. The fifth step and the sixth step may be carried out in any order.

As illustrated in FIG. 4(c), in the first step, a seventh step of configuring the laminated body 40 by laminating the first structure P1 and the second structure P2 on each other is subsequently carried out. In the seventh step, the first structure P1 is bonded to the second structure P2 by the adhesive layer 17 such that the inorganic layer 15 is interposed between the third surface 13b of the first flexible support body 13 and the fourth surface 14a of the second flexible support body 14. Here, the inorganic layer 15 is bonded to the third surface 13b.

As illustrated in FIG. 5(a), in the first step, an eighth step of providing the protective layers 18 and 19 with respect to the laminated body 40 is subsequently carried out. In the eighth step, the protective layer 18 is formed first on the surface of the scintillator layer 12 on the side opposite to the support body 11 (one surface of the laminated body 40). In the eighth step, the protective layer 19 is subsequently formed so as to cover the entire laminated body 40 and the entire protective layer 18. The scintillator panel 10 is prepared as a result.

Meanwhile, in the second step, the sensor panel 20 is prepared as illustrated in FIG. 5(b). The adhesive layer 23 is provided on the mounting surface 21 of the sensor panel 20 via the protective layer 22.

After the first and second steps, the third step of mounting the scintillator panel 10 on the sensor panel 20 is carried out as illustrated in FIG. 6(a). In the third step, the scintillator panel 10 is mounted on the sensor panel 20 via the adhesive layer 23. More specifically, in the third step, the scintillator panel 10 is provided on the sensor panel 20 such that the first surface 11a is on the sensor panel 20 side with respect to the second surface 11b of the support body 11. In other words, the surface of the scintillator layer 12 on the side opposite to the support body 11 is bonded to the mounting surface 21 by the adhesive layer 23 (via the protective layers 18, 19, and 22) in a state where the scintillator layer 12 faces the mounting surface 21.

Subsequently, the fourth step of providing the resin frame 30 across the scintillator panel 10 and the sensor panel 20 is carried out as illustrated in FIG. 6(b). In the fourth step, a dispenser 50 is disposed around the scintillator panel 10, resin 51 is applied around the scintillator panel 10, the applied resin 51 is cured, and the resin frame 30 is formed as a result. Here, the resin application and curing are performed (via the protective layer 19) with respect to the mounting surface 21, the first side surface 11s of the support body 11, and the second side surface 12s of the scintillator layer 12. As a result, the resin frame 30 is formed so as to extend from the mounting surface 21 onto the first side surface 11s when viewed in the first direction intersecting with the first side surface 11s and the second side surface 12s. As a result, the scintillator layer 12 is sealed by the resin frame 30 and the radiation detector 1 is manufactured.

In the fourth step in particular, the resin frame 30 is formed so as to extend from the mounting surface 21 to the fourth surface 14a of the second flexible support body 14 beyond the inorganic layer 15 when viewed in the first direction and the inorganic layer 15 is further sealed as a result. Further, in the fourth step, the resin frame 30 is formed so as to extend from the mounting surface 21 to the peripheral edge portion of the second surface 11b of the support body 11. This can be realized by, for example, forming the main body portion 31 of the resin frame 30 by performing the application (and the subsequent curing) of the resin 51 while the dispenser 50 moves in a circle along the peripheral edge of the second surface 11b outside the second surface 11b and then forming the extending portion 32 by performing the application (and the subsequent curing) of the resin 51 while the dispenser 50 moves in a circle along the peripheral edge of the second surface 11b inside the second surface 11b. Alternatively, the resin frame 30 can be formed by performing overall curing after forming a part corresponding to the main body portion 31 of the resin frame 30 by performing the application of the resin 51 while the dispenser 50 moves in a circle along the peripheral edge of the second surface 11b outside the second surface 11b and forming a part corresponding to the extending portion 32 using the sagging of the resin from the part into the second surface 11b.

It should be noted that the resin frame 30 is formed in the fourth step by the application and curing of the resin 51 being performed a plurality of times. In particular, the application and curing of the resin 51 are performed a plurality of times regarding the formation of the main body portion 31 as well. As a result, the overlapping portion 30d of the part 30a and the part 30b is formed by the resin 51 being applied and cured once and then the resin 51 being applied and cured with respect to the resin frame 30 (main body portion 31).

As described above, in the radiation detector 1 according to the present embodiment, the scintillator panel 10 is mounted on the sensor panel 20 such that the scintillator layer 12 faces the mounting surface 21 of the sensor panel 20. As for the scintillator panel 10 in particular, the first side surface 11s as the side surface of the support body 11 and the second side surface 12s as the side surface of the scintillator layer 12 are positioned on the same plane. In other words, the scintillator layer 12 is provided on the entire surface of the support body 11 when viewed in the direction intersecting with the first surface 11a and the second surface 11b of the support body 11 and an increase in effective area is achieved as a result.

Meanwhile, in such a configuration, the boundary between the support body 11 and the scintillator layer 12 and the boundary between the scintillator layer 12 and the sensor panel 20 are prone to lateral damage. On the other hand, in the radiation detector 1, the resin frame 30 extends at least from the mounting surface 21 of the sensor panel 20 onto the first side surface 11s of the support body 11, and thus the scintillator layer 12 is sealed. Accordingly, damage to the boundary and the second side surface 12s as the side surface of the scintillator layer 12 can be avoided. At the same time, the dampproofness of the scintillator layer 12 is improved and peeling attributable to a difference in thermal expansion and warpage is suppressed. In other words, with the radiation detector 1, reliability is ensured while an increase in effective area is achieved as described above.

In addition, in the radiation detector 1, the support body 11 has the first flexible support body 13 having the first surface 11a and the third surface 13b on the side opposite to the first surface 11a, the second flexible support body 14 having the second surface 11b and the fourth surface 14a on the side opposite to the second surface 11b, and the inorganic layer 15 provided between the third surface 13b and the fourth surface 14a. The resin frame 30 further seals the inorganic layer 15 by extending at least from the mounting surface 21 to the fourth surface 14a when viewed in the first direction.

Accordingly, the inorganic layer 15 suppresses moisture infiltration from the second surface 11b side into the scintillator layer 12 via the first flexible support body 13. In particular, the dampproofness is reliably improved by the resin frame 30 extending beyond the inorganic layer 15 (so as to reach the fourth surface 14a). Further, the second flexible support body 14 protects the inorganic layer 15 from contact and suppresses deterioration of the inorganic layer 15. As a result, reliability is reliably ensured.

In addition, in the radiation detector 1, the resin frame 30 extends from the mounting surface 21 to the peripheral edge portion of the second surface 11b. Accordingly, the dampproofness is further improved, the peeling is reliably suppressed, and reliability is ensured more reliably.

In addition, in the radiation detector 1, the resin frame 30 includes the inner edge 33 positioned on the second surface 11b and the outer edge 34 positioned outside the second surface 11b when viewed in the second direction intersecting with the second surface 11b. The distance S33 from the inner edge 33 of the resin frame 30 to the peripheral edge E of the second surface 11b is twice or less the distance S34 from the peripheral edge E of the second surface 11b to the outer edge 34. Accordingly, reliability can be reliably ensured and a decrease in effective area can be suppressed at the same time.

In addition, in the radiation detector 1, the resin frame 30 includes the plurality of parts arranged along the first side surface 11s and the second side surface 12s and includes the at least one overlapping portion 30d where the parts 30a and 30b overlap. The resin frame may be configured by the plurality of parts in this manner.

In addition, in the radiation detector 1, the ratio of the width W30 of the resin frame 30 from the first side surface 11s is 0.1 or more and 12.5 or less when the height H30 of the resin frame 30 from the mounting surface 21 is 1. Accordingly, reliability can be ensured and an increase in size can be avoided at the same time.

In addition, the radiation detector 1 is provided with the adhesive layer 23 interposed between the mounting surface 21 and the scintillator panel 10 and bonding the sensor panel 20 and the scintillator panel 10 to each other. The scintillator panel 10 and the sensor panel 20 may be joined by bonding in this manner.

In addition, in the radiation detector 1, the resin frame 30 may include a filler material made of an inorganic material. The dampproofness is improved in this case. In addition, the resin frame 30 may contain at least a pigment having reflectivity or absorbency with respect to the scintillation light generated by the scintillator layer 12. Optical characteristics are improved in this case.

In addition, in the radiation detector 1, the protective layer 22 is formed on the mounting surface 21. Accordingly, the reliability of the sensor panel is improved. Further, in the radiation detector 1, the scintillator panel 10 includes the protective layer 19 formed on the first side surface 11s and the second side surface 12s. Accordingly, lateral damage and moisture infiltration can be suppressed more reliably.

In the method for manufacturing the radiation detector 1 according to the present embodiment, the scintillator panel 10 is mounted on the sensor panel 20 such that the scintillator layer 12 faces the mounting surface 21 of the sensor panel 20. As for the scintillator panel 10 in particular, the first side surface 11s as the side surface of the support body 11 and the second side surface 12s as the side surface of the scintillator layer 12 are positioned on the same plane. In other words, the scintillator layer 12 is provided on the entire surface of the support body 11 when viewed in the second direction and an increase in effective area is achieved as a result.

In such a configuration, the boundary between the support body 11 and the scintillator layer 12 and the boundary between the scintillator layer 12 and the sensor panel 20 are prone to lateral damage. On the other hand, in this manufacturing method, the resin frame 30 is formed so as to seal the scintillator layer 12 by extending at least from the mounting surface 21 of the sensor panel 20 onto the first side surface 11s of the support body 11. Accordingly, damage to the boundary and the second side surface 12s as the side surface of the scintillator layer 12 can be avoided. At the same time, the dampproofness of the scintillator layer 12 is improved and peeling attributable to a difference in thermal expansion and warpage is suppressed. In other words, by this manufacturing method, it is possible to manufacture the reliable radiation detector 1 while achieving an increase in effective area as described above.

In addition, in the fourth step of the manufacturing method according to the present embodiment, the resin frame 30 may be formed by the resin 51 being applied and cured a plurality of times. In this case, the overlapping portion 30d of the plurality of parts 30a and 30b configuring the resin frame 30 can be formed by the resin 51 being applied and cured after the resin 51 is applied and cured once.

One form of the present disclosure has been described in the above embodiment. Accordingly, the present disclosure is not limited to the above embodiment and various modifications can be made.

For example, in the fourth step of the method for manufacturing the radiation detector 1, the resin frame 30 can be formed by the resin 51 being applied and cured using a mold disposed on the mounting surface 21 so as to surround the scintillator panel 10 while being separated from the scintillator panel 10 when viewed in the second direction intersecting with the second surface 11b of the support body 11. In this case, the generation of a sagging portion of the resin 51 can be suppressed. It should be noted that the formation of the resin frame 30 in the fourth step is not limited to the resin 51 being applied and cured a plurality of times and may be performed by the resin 51 being applied and cured once.

Further, in the radiation detector 1, the configuration of the support body 11 is any configuration not limited to the laminated structure of the first flexible support body 13, the inorganic layer 15, and the second flexible support body 14.

INDUSTRIAL APPLICABILITY

According to the present disclosure, a radiation detector and a radiation detector manufacturing method enabling reliability to be ensured and an increase in effective area to be achieved at the same time are provided.

REFERENCE SIGNS LIST

1: radiation detector, 10: scintillator panel, 11: support body, 11a: first surface, 11b: second surface, 11s: first side surface, 12: scintillator layer, 12s: second side surface, 13: first flexible support body, 13b: third surface, 14: second flexible support body, 14a: fourth surface, 15: inorganic layer, 16, 17, 23: adhesive layer, 18, 19, 22: protective layer, 20: sensor panel, 21: mounting surface, 30: resin frame, 33: inner edge, 34: outer edge.

The invention claimed is:

1. A radiation detector comprising:
a sensor panel;
a scintillator panel; and
a resin frame provided across the sensor panel and the scintillator panel, wherein
the sensor panel has a mounting surface where the scintillator panel is mounted,
the scintillator panel includes
a support body having a first surface, a second surface on a side opposite to the first surface, and a first side surface connecting the first surface and the second surface to each other, and
a scintillator layer formed on the first surface and containing a plurality of columnar crystals,
the scintillator panel is mounted on the mounting surface such that the scintillator layer and the first surface face the mounting surface,
the scintillator layer has a second side surface extending so as to be positioned on the same plane as the first side surface,
the resin frame is configured to seal the scintillator layer by extending at least from the mounting surface onto the first side surface when viewed in a first direction intersecting with the first side surface and the second side surface, and
the resin frame extends from the mounting surface to a peripheral edge portion of the second surface.

2. A radiation detector comprising:
a sensor panel;
a scintillator panel; and
a resin frame provided across the sensor panel and the scintillator panel, wherein
the sensor panel has a mounting surface where the scintillator panel is mounted,
the scintillator panel includes
a support body having a first surface, a second surface on a side opposite to the first surface, and a first side surface connecting the first surface and the second surface to each other, and
a scintillator layer formed on the first surface and containing a plurality of columnar crystals,
the scintillator panel is mounted on the mounting surface such that the scintillator layer and the first surface face the mounting surface,
the scintillator layer has a second side surface extending so as to be positioned on the same plane as the first side surface,
the resin frame is configured to seal the scintillator layer by extending at least from the mounting surface onto the first side surface when viewed in a first direction intersecting with the first side surface and the second side surface,
the support body has
a first flexible support body having the first surface and a third surface on the side opposite to the first surface,
a second flexible support body having the second surface and a fourth surface on a side opposite to the second surface, and
an inorganic layer provided between the third surface and the fourth surface, and
the resin frame is configured to seal the inorganic layer by extending at least from the mounting surface to the fourth surface when viewed in the first direction.

3. The radiation detector according to claim 2, wherein the resin frame includes an inner edge positioned on the second surface and an outer edge positioned outside the second surface when viewed in a second direction intersecting with the second surface, and
a distance from the inner edge of the resin frame to a peripheral edge of the second surface is twice or less a distance from the peripheral edge of the second surface to the outer edge.

4. The radiation detector according to claim 1, wherein the resin frame includes a plurality of parts arranged along the first side surface and the second side surface and includes at least one overlapping portion where one of the parts and another of the parts overlap.

5. A radiation detector comprising:
a sensor panel;
a scintillator panel; and
a resin frame provided across the sensor panel and the scintillator panel, wherein
the sensor panel has a mounting surface where the scintillator panel is mounted,
the scintillator panel includes
a support body having a first surface, a second surface on a side opposite to the first surface, and a first side surface connecting the first surface and the second surface to each other, and
a scintillator layer formed on the first surface and containing a plurality of columnar crystals,
the scintillator panel is mounted on the mounting surface such that the scintillator layer and the first surface face the mounting surface,
the scintillator layer has a second side surface extending so as to be positioned on the same plane as the first side surface,
the resin frame is configured to seal the scintillator layer by extending at least from the mounting surface onto the first side surface when viewed in a first direction intersecting with the first side surface and the second side surface, and
a ratio of a width of the resin frame from the first side surface is 0.1 or more and 12.5 or less when a height of the resin frame from the mounting surface is 1.

6. The radiation detector according to claim 1, comprising an adhesive layer interposed between the mounting surface and the scintillator panel and bonding the sensor panel and the scintillator panel to each other.

7. The radiation detector according to claim 1, wherein the resin frame contains a filler material made of an inorganic material.

8. A radiation detector comprising:
a sensor panel;
a scintillator panel; and
a resin frame provided across the sensor panel and the scintillator panel, wherein
the sensor panel has a mounting surface where the scintillator panel is mounted,
the scintillator panel includes
a support body having a first surface, a second surface on a side opposite to the first surface, and a first side surface connecting the first surface and the second surface to each other, and
a scintillator layer formed on the first surface and containing a plurality of columnar crystals, the scintillator panel is mounted on the mounting surface such that the scintillator layer and the first surface face the mounting surface, the scintillator layer has a second side surface extending so as to be positioned on the same plane as the first side surface, the resin frame is configured to seal the scintillator layer by extending at least from the mounting surface onto the first side surface when viewed in a first direction intersecting with the first side surface and the second side surface, and the resin frame contains at least a pigment having reflectivity or absorbency with respect to scintillation light generated by the scintillator layer.

9. The radiation detector according to claim 1, wherein a protective layer is formed on the mounting surface.

10. The radiation detector according to claim 1, wherein the scintillator panel includes a protective layer formed on the first side surface and the second side surface.

11. A radiation detector manufacturing method comprising:
a first step of preparing a scintillator panel having a support body and a scintillator layer formed on the support body;
a second step of preparing a sensor panel including a photoelectric conversion element;
a third step of mounting the scintillator panel on the sensor panel such that the scintillator layer faces the sensor panel; and
a fourth step of providing a resin frame across the sensor panel and the scintillator panel after the third step, wherein
the support body has a first surface where the scintillator layer is formed, a second surface on a side opposite to the first surface, and a first side surface connecting the first surface and the second surface to each other,
the scintillator layer has a second side surface extending so as to be positioned on the same plane as the first side surface,
the sensor panel has a mounting surface where the scintillator panel is mounted, and
in the fourth step, the resin frame is formed by resin application and curing being performed with respect to at least the mounting surface, the first side surface, and the second side surface and so as to seal the scintillator layer by extending at least from the mounting surface onto the first side surface when viewed in a first direction intersecting with the first side surface and the second side surface, and extending from the mounting surface to a peripheral edge portion of the second surface.

12. The radiation detector manufacturing method according to claim 11, wherein, in the fourth step, the resin frame is formed by the resin application and curing being performed a plurality of times.

13. The radiation detector manufacturing method according to claim 11, wherein, in the fourth step, the resin frame is formed by the resin application and curing being performed using a mold disposed on the mounting surface so as to surround the scintillator panel while being separated from the scintillator panel when viewed in a second direction intersecting with the second surface.

14. The radiation detector manufacturing method according to claim 11, wherein, in the third step, the scintillator panel is mounted on the sensor panel via an adhesive layer.

* * * * *